US00PP20908P2

(12) United States Plant Patent
Sakazaki

(10) Patent No.: US PP20,908 P2
(45) Date of Patent: Mar. 30, 2010

(54) *CALIBRACHOA* PLANT NAMED 'USCALI99M'

(50) Latin Name: ***Calibrachoa* sp.**
Varietal Denomination: USCALI99M

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 12/291,546

(22) Filed: Nov. 12, 2008

(51) Int. Cl.
*A01H 5/00* (2006.01)

(52) U.S. Cl. ..... Plt./413

(58) Field of Classification Search ..... Plt./263, Plt./413

See application file for complete search history.

*Primary Examiner*—Susan B McCormick Ewoldt
(74) *Attorney, Agent, or Firm*—C. A. Whealy

(57) ABSTRACT

A new and distinct cultivar of *Calibrachoa* plant named 'USCALI99M', characterized by its compact, mounding and outwardly spreading to semi-trailing growth habit; numerous yellow-colored flowers with purple-colored flecking and venation; and good garden performance.

1 Drawing Sheet

Botanical designation: *Calibrachoa* sp.
Cultivar denomination: 'USCALI99M'

BACKGROUND OF THE INVENTION

The present invention relates to a new and distinct cultivar of *Calibrachoa* plant, botanically known as *Calibrachoa* sp. and hereinafter referred to by the name 'USCALI99M'.

The new *Calibrachoa* plant is a naturally-occurring branch mutation of a *Calibrachoa* sp. 'USCALI99', disclosed in U.S. Plant Pat. No. 17,679. The new *Calibrachoa* was discovered and selected by the Inventor on a single plant from within a population of plants of 'USCALI99' in a controlled greenhouse environment in Carlton, Mich. on June 20, 2006.

Asexual reproduction of the new *Calibrachoa* plant by vegetative cuttings in a controlled greenhouse environment in Carlton, Mich. since Jun. 20, 2006, has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USCALI99M'. These characteristics in combination distinguish 'USCALI99M' as a new and distinct cultivar of *Calibrachoa:*

1. Compact, mounding and outwardly spreading to semi-trailing growth habit.
2. Numerous yellow-colored flowers with purple-colored flecking and venation.
3. Good garden performance.

The new *Calibrachoa* can be compared to plants of the female parent, 'USCALI99'. Plants of the new *Calibrachoa* differ primarily from plants of 'USCALI99' in flower color as plants of 'USCALI99' have purple-colored flowers.

Plants of the new *Calibrachoa* can be compared to plants of 'Caltrablupu', disclosed in U.S. Plant Pat. No. 18,930. Plants of the new *Calibrachoa* differ from plants of 'Caltrablupu' in the following characteristics:

1. Plants of the new *Calibrachoa* are not as trailing as plants of 'Caltrablupu'.
2. Plants of the new *Calibrachoa* have larger flowers than plants of 'Caltrablupu'.
3. Plants of the new *Calibrachoa* and 'Caltrablupu' differ in flower color as plants of 'Caltrablupu' have dark purple-colored flowers.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.* The photograph at the bottom of the sheet comprises a side perspective view of a typical flowering plant of 'USCALI99M' grown in a container. The photograph at the top of the sheet comprises a close-up of typical flowers, flower buds and leaves of 'USCALI99M'.

DETAILED BOTANICAL DESCRIPTION

The aforementioned photographs and following observations, measurements and values describe plants grown in Bonsall, Calif., under commercial practice during the summer and autumn in an outdoor nursery with day temperatures ranging from 18° C. to 38° C. and night temperatures ranging from 13° C. to 24° C. Rooted young plants had been growing for ten weeks when the photographs and description were taken. In the following description, color references are made to The Royal Horticultural Society Colour Chart, 2001 Edition, except where general terms of ordinary dictionary significance are used.

Botanical classification: *Calibrachoa* sp. 'USCALI99M'.

Parentage: Naturally-occurring branch mutation of *Calibrachoa* sp. 'USCALI99', disclosed in U.S. Plant Pat. No. 17,679.

Propagation:

*Type.*—By vegetative cuttings.

*Time to produce a rooted young plant, summer.*—About three weeks at temperatures of 20° C.

*Time to produce a rooted young plant, winter.*—About four weeks at temperatures of 20° C.

*Root description.*—Fine; white in color.

*Rooting habit.*—Freely branching; dense.

Plant description:

*Plant and growth habit.*—Compact, mounding and outwardly spreading to semi-trailing plant habit. Freely branching habit with about seven to eight primary lateral branches each with multiple secondary lateral branches; pinching enhances branching; vigorous growth habit.

*Plant height.*—About 12 cm.

*Plant diameter.*—About 64 cm.

Lateral branch description:

*Length.*—About 34 cm.

*Diameter.*—About 3 mm.

*Internode length.*—About 1.8 cm.

*Strength.*—Strong.

*Aspect.*—Initially upright to outwardly spreading to semi-trailing.

*Texture.*—Pubescent.

*Color.*—Close to 145A; towards the base, close to 197A.

Foliage description:

*Arrangement.*—Before flowering, alternate, simple; after flowering, opposite, simple.

*Length.*—About 3 cm.

*Width.*—About 1 cm.

*Shape.*—Elliptical.

*Apex.*—Broadly acute to rounded.

*Base.*—Attenuate.

*Margin.*—Entire.

*Texture, upper and lower surfaces.*—Pubescent.

*Venation pattern.*—Pinnate; arcuate.

*Color.*—Developing leaves, upper and lower surfaces: Close to 146B. Fully expanded leaves, upper surface: Close to 147A; venation, close to 146B. Fully expanded leaves, lower surface: Close to 147B; venation, close to 147C.

*Petiole.*—Length: About 4 mm. Diameter: About 2 mm. Texture, upper and lower surfaces: Pubescent. Color, upper surface: Close to 146C. Color, lower surface: Close to 147D.

Flower description:

*Flower arrangement and habit.*—Single salverform flowers arising from leaf axils. Freely flowering habit with usually about 26 to 27 open flowers and flower buds per lateral branch. Flowers face upright to mostly outwardly.

*Fragrance.*—None detected.

*Natural flowering season.*—Plants of the new *Calibrachoa* initiate and develop flowers about four to six weeks after planting. Plants flower continuously from April to September in Southern California; flowers persistent.

*Flower longevity.*—Individual flowers last about three to four days on the plant.

*Flower diameter.*—About 2.8 cm by 3 cm.

*Flower length* (*height*).—About 2.8 cm.

*Flower throat diameter.*—About 5 mm by 8 mm.

*Flower tube diameter, base.*—About 4 mm.

*Flower tube length.*—About 2 cm.

*Flower bud.*—Shape: Elongated oblong. Length: About 2.5 cm. Diameter: About 8 mm. Color: Close to 11C tinted with close to N77D.

*Corolla.*—Arrangement: Five petals fused at the base and opening into a flared trumpet. Petal length from throat: About 1.2 cm. Petal lobe width: About 1.4 cm. Petal shape: Roughly spatulate. Petal apex: Mucronate to cuspidate. Petal margin: Entire. Petal texture, upper surface: Smooth, glabrous; velvety. Petal texture, lower surface: Scattered pubescence. Throat texture: Smooth, glabrous. Tube texture: Pubescent. Color: Petal, when opening, upper surface: Close to 11D; venation, close to 183D. Petal, when opening, lower surface: Close to 11D; venation, close to 185C. Petal, fully opened, upper surface: Ground color, close to 16C; random flecking, close to N79B to N79C; venation, close to N79A. Petal, fully opened, lower surface: Close to N79D; venation, close to 79A. Throat: Close to 11A to 11B; venation, close to N79B. Tube: Close to 11B; random flecking, close to N79C; venation, close to 79A.

*Calyx.*—Arrangement: One star-shaped calyx tube with five sepals fused at the base. Sepal length: About 1.4 cm. Sepal width: About 2.5 mm. Sepal shape: Lanceolate. Sepal apex: Acute. Sepal margin: Entire. Sepal texture, upper and lower surfaces: Pubescent. Color, upper and lower surfaces: Close to 146A.

*Peduncles.*—Length: About 2.2 cm. Diameter: About 1 mm. Angle: About 45° from stem axis. Strength: Strong. Texture: Pubescent. Color: Close to 146B.

*Reproductive organs.*—Stamens: Quantity/arrangement: About five per flower. Anther shape: Oval. Anther length: About 1 mm. Anther color: Close to 11A. Pollen amount: Scarce. Pollen color: Close to 7A. Pistils: Quantity: One per flower. Pistil length: About 1.2 cm. Style length: About 9 mm. Style color: Close to 144C. Stigma shape: Rounded, flattened. Stigma color: Close to 144B. Ovary color: Close to 145C. Seed/fruit: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'USCALI99M' as illustrated and described.

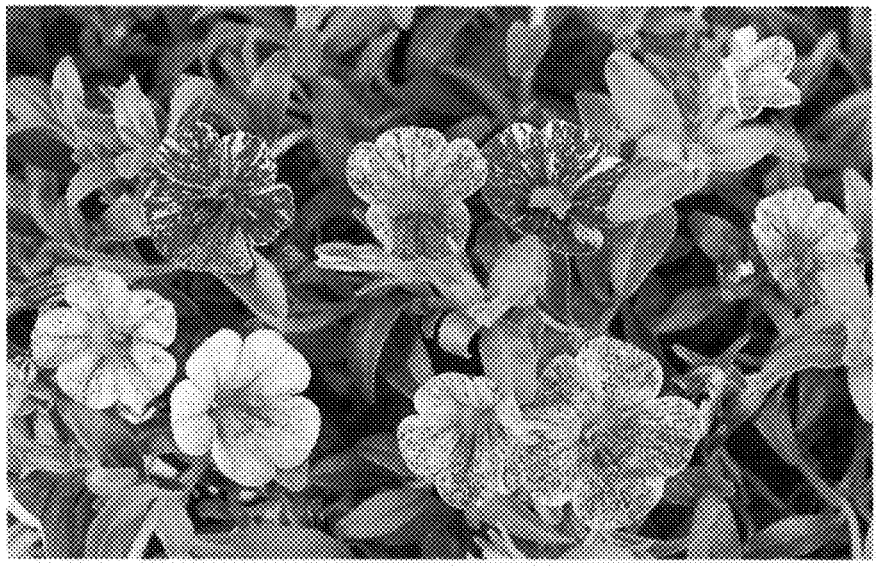
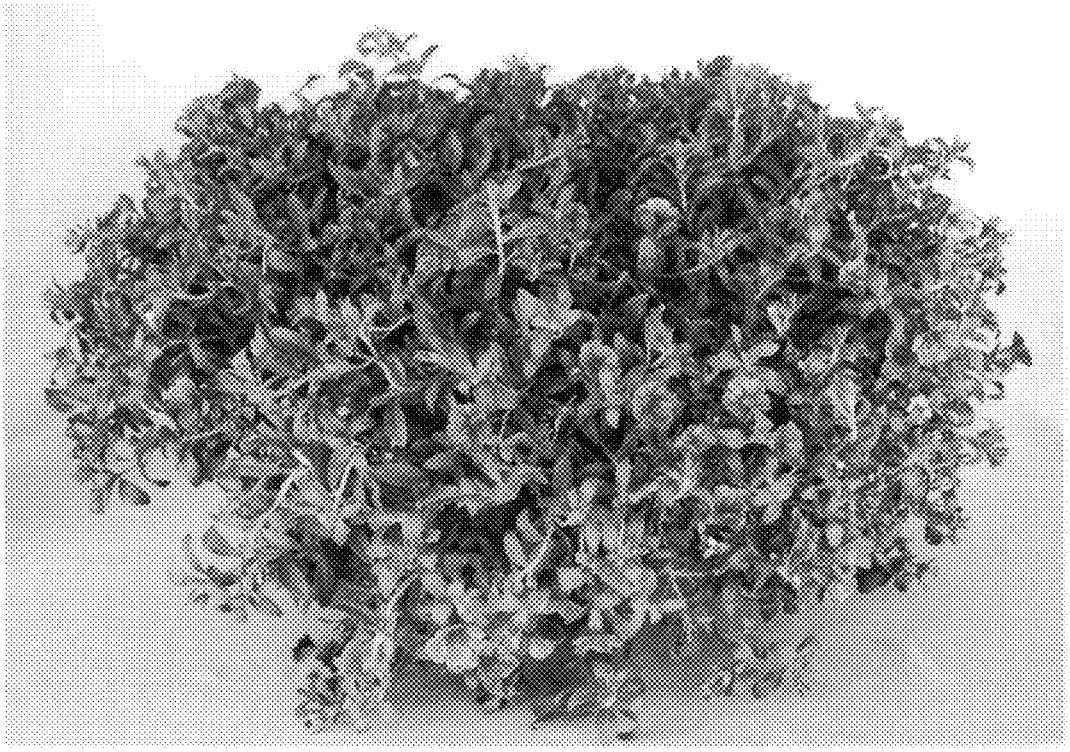

* * * * *